United States Patent
Patwardhan (10) Patent No.: US 10,054,603 B2
(45) Date of Patent: Aug. 21, 2018

(54) SYSTEMS AND METHODS FOR REAGENTLESS TEST STRIPS

(71) Applicant: Polymer Technology Systems, Inc., Indianapolis, IN (US)

(72) Inventor: Aniruddha Patwardhan, Fishers, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 0 days.

(21) Appl. No.: 15/254,804

(22) Filed: Sep. 1, 2016

(65) Prior Publication Data

US 2017/0059596 A1   Mar. 2, 2017

Related U.S. Application Data

(60) Provisional application No. 62/212,994, filed on Sep. 1, 2015.

(51) Int. Cl.
| | |
|---|---|
| G01N 21/77 | (2006.01) |
| G01N 21/75 | (2006.01) |
| G01N 33/52 | (2006.01) |
| G01N 33/92 | (2006.01) |
| C12M 3/00 | (2006.01) |
| G01N 21/78 | (2006.01) |
| B01L 3/00 | (2006.01) |

(52) U.S. Cl.
CPC .............. *G01N 33/92* (2013.01); *B01L 3/502* (2013.01); *G01N 21/78* (2013.01); *G01N 33/525* (2013.01); *B01L 2300/0654* (2013.01); *B01L 2300/0825* (2013.01); *B01L 2300/0838* (2013.01); *B01L 2300/0887* (2013.01); *G01N 2021/752* (2013.01); *G01N 2021/7759* (2013.01)

(58) Field of Classification Search
CPC ..... G01N 2021/7759; G01N 2021/752; G01N 33/525; G01N 33/92; B01L 2300/0825
USPC ......... 435/287.7, 287.8, 287.1, 288.3, 288.4, 435/299.7
See application file for complete search history.

(56) References Cited

U.S. PATENT DOCUMENTS

| | | | |
|---|---|---|---|
| 2009/0303477 A1* | 12/2009 | Burd | .......................... G01J 3/02 356/326 |
| 2013/0217054 A1 | 8/2013 | Huffstodt et al. | |
| 2014/0255958 A1 | 9/2014 | Kim et al. | |
| 2015/0030504 A1 | 1/2015 | Pang et al. | |

OTHER PUBLICATIONS

International Search Report and Written Opinion dated Nov. 16, 2016, issued in co-pending PCT App. No. PCT/US2016/049954 (13 pages).
Oncescu, V. et al., "Cholesterol testing on a smartphone," Lab Chip, vol. 14, pp. 759-763, 2014; abstract; pp. 759-761; figure 3.

* cited by examiner

*Primary Examiner* — Scott Long
*Assistant Examiner* — Paul C Martin
(74) *Attorney, Agent, or Firm* — Woodard, Emhardt, Moriarty, McNett & Henry LLP (57) ABSTRACT

A system for detecting an analyte with a reagentless dry test strip includes a collector for collecting a blood sample from a user. The system additionally includes a mixer for receiving the collector and mixing the blood sample. The system additionally includes reagents, located in the mixer, for mixing with the blood sample. The system additionally includes a dry test strip for receiving the blood sample mixed with the reagents.

10 Claims, 12 Drawing Sheets

SYSTEMS AND METHODS FOR REAGENTLESS TEST STRIPS

CROSS REFERENCE TO RELATED APPLICATIONS

This application claims the benefit of U.S. Provisional Application No. 62/212,994, filed on Sep. 1, 2015, which is incorporated herein by reference in its entirety.

BACKGROUND

Blood testing for analytes, diseases, infections, and other conditions that may be detected via blood analysis is a useful diagnostic tool. A useful point-of-care diagnostic tool is a dry test strip. A major cost in making such test strips is the active enzymes and chromophores. It would be ideal if the amount of active enzymes or chromophores and other components needed in the preparation of test strips for analytes detection could be reduced.

BRIEF SUMMARY

In one embodiment, a system for detecting an analyte with a reagentless dry test strip includes a collector for collecting a blood sample from a user. The system additionally includes a mixer for receiving the collector and mixing the blood sample. The system additionally includes reagents, located in the mixer, for mixing with the blood sample. The system additionally includes a dry test strip for receiving the blood sample mixed with the reagents. Optionally, the system further includes an optical meter for detecting a color change in the test strip, the optical meter executing instructions stored in a fixed tangible medium in the optical meter, the instructions, when executed by the optical meter, causing the optical meter to detect an optical property of the test strip and report a level of an analyte in the blood sample based on the optical property. Optionally, the collector includes a capillary tube. Alternatively, the mixer is shaped to seal with the collector when the collector is inserted into the mixer. In one configuration, the dry test strip includes a spreading layer. In another configuration, the dry test strip includes a first red blood cell separation layer. Optionally, the dry test strip includes a second red blood cell separation layer. Alternatively, the dry test strip includes a reaction membrane. In one configuration, the reaction membrane does not include any reagents. In another configuration, the reagents provide for the testing of total cholesterol. Optionally, the reagents include cholesterol esterase, cholesterol oxidase, horseradish peroxidase, and quinoneimine chromophore precursors like 4-amino antipyrine (4-AAP) and N-Ethyl-N-(2-hydroxy-3-sulfopropyl)-3,5-dimethylaniline, sodium salt, and monohydrate (MAOS).

In one embodiment, a method for detecting an analyte with a reagentless dry test strip includes providing a collector, a mixer, reagents located in the mixer, and a dry test strip, and using the collector to collect a blood sample. The method further includes mating the collector with the mixer and mixing the blood sample in the mixer. The method further includes dosing the blood sample from the mixer to the dry test strip. The method further includes detecting an optical property in the test strip with an optical meter. Optionally, the mating includes inserting the collector into the mixer. In one configuration, the method further includes correlating the optical property of the test strip to a predicted concentration of analyte in the blood sample and reporting a level of an analyte in the blood sample based on the optical property. Optionally, the collector includes a capillary tube. Alternatively, the mixer is shaped to seal with the collector when the collector is inserted into the mixer. Optionally, the dry test strip includes a spreading layer. In one configuration, the dry test strip includes a first red blood cell separation layer. Optionally, the dry test strip includes a second red blood cell separation layer. Alternatively, the dry test strip includes a reaction membrane. Optionally, the reaction membrane does not include any reagents. In one configuration, the reagents provide for the testing of total cholesterol. Optionally, the reagents include cholesterol esterase, cholesterol oxidase, horseradish peroxidase, and quinoneimine chromphore precursors like 4-amino antipyrine (4-AAP) and N-Ethyl-N-(2-hydroxy-3-sulfopropyl)-3,5-dimethylaniline, sodium salt, and monohydrate (MAOS).

DETAILED DESCRIPTION

Certain terminology is used herein for convenience only and is not to be taken as a limitation on the embodiments of the systems and methods for reagentless test strips. In the drawings, the same reference letters are employed for designating the same elements throughout the several figures. Systems and methods for reagentless test strips include a premix step in a handheld mixer where reaction occurs prior to dosing on a reagentless dry test strip. Since the mixing in this process is more complete and less preservatives are required, the usage of available reagent is also more complete as compared to a dry test strip process.

Dry test strip systems (including CardioChek® test strips) typically use a dry test strip chemistry format, where the membranes are impregnated with expensive formulary. The main components in the formulary are the expensive enzymes which are added 10 to 30 times in excess to ensure there is sufficient "active" enzyme molecules (over the life of the lot) to confer reactivity to the substrate to yield a reaction and, thus, color development (often using the Trinder reaction). In addition, costly chromophores generating precursors, stabilizers, and dye mortants are added to maintain the stability and smooth color development of the test strip when dosed with a whole blood sample. A typical system includes a spreading layer, one or more layers for separating hematocrit and unselected analytes, and a reaction layer. The most costly elements of the test strip typically are found in the reaction layer and the separation layers.

Systems and methods for reagentless test strips offer significant reduction in enzyme usage by not impregnating the reaction membrane, but using the dry test strip format to interrogate the color developed using the reflectance methodology. Advantages include:

1. Significantly less enzymes will be used per test, thus significantly reducing cost per test.
2. Reduction in strip-to-strip variation due to inconsistent impregnation methods on the membrane.
3. Will eliminate expensive in-process membrane checks to ensure if the impregnated membranes meet quality control criteria.

Figure 1A:
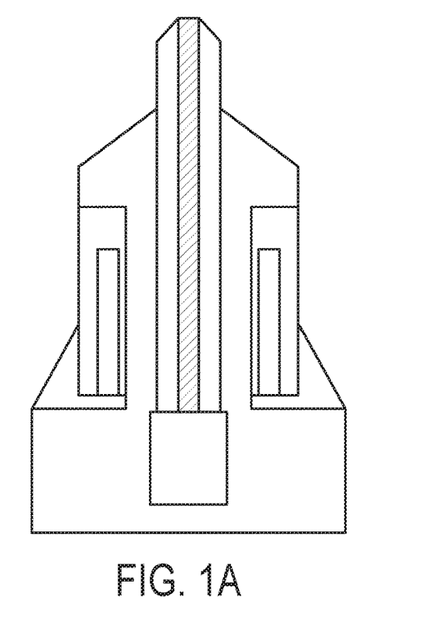
FIGS. 1a and 1b show one embodiment of a sample collector with whole blood and the method for collecting capillary whole blood from a finger stick.
Figure 1B:
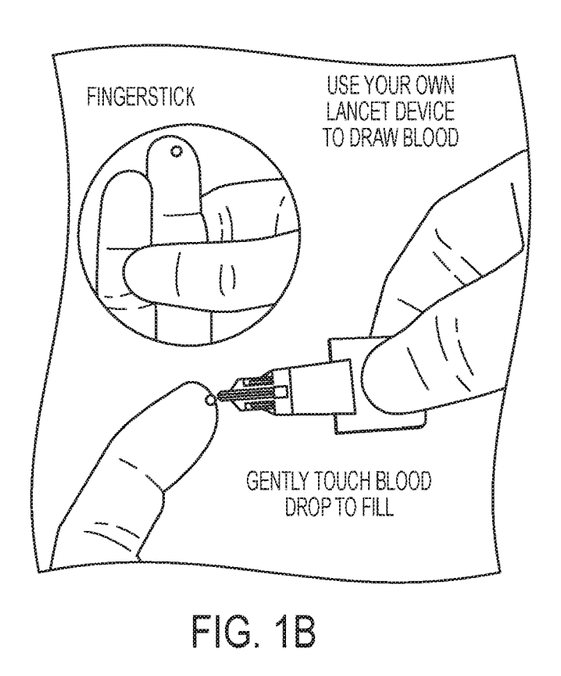
Figure 2:
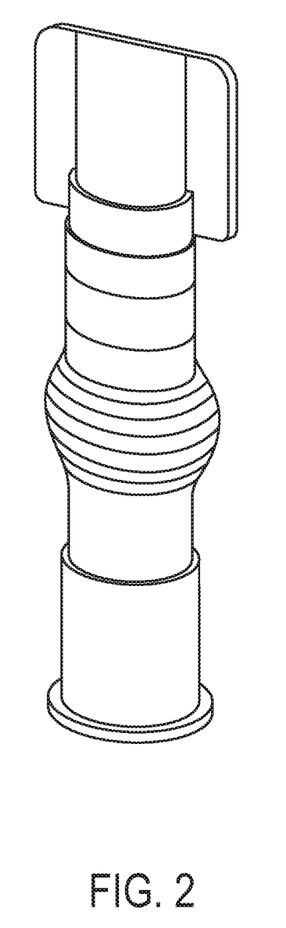
FIG. 2 shows the sample collector of FIG. 1a inserted into one embodiment of the mixer containing reagents.

The samples (capillary or venous whole blood) will be collected by a collector as shown in FIGS. 1a and 1b, and placed in a mixer as shown in FIG. 2. FIGS. 1a and 1b show one embodiment of a sample collector with whole blood and the method for collecting capillary whole blood from a finger stick. FIG. 2 shows the sample collector inserted into the mixer containing reagents. Alternatively, the sample collector may include a cap or other closure device for providing for a seal during mixing. In one alternative, the sample collector may include a lancet as well as a capillary tube. The mixer portion contains appropriate enzymes (e.g., for a total cholesterol assay, the enzyme train of cholesterol esterase, cholesterol oxidase, horseradish peroxidase, and quinoneimine chromphore precursors like 4-amino antipyrine (4-AAP) and N-Ethyl-N-(2-hydroxy-3-sulfopropyl)-3,5-dimethylaniline, sodium salt, and monohydrate (MAOS) in a proprietary formulary for a specific analyte). The whole blood or serum sample is mixed with the enzyme system in the liquid form for a specific time and then dosed on a test strip (for example, a CardioChek® strip (single test strip)) and read on an optical analyzer (e.g., a CardioChek® analyzer). Although a formulary for total cholesterol is provided, a variety of analytes may be tested according to this method, including, but not limited to, total cholesterol, LDL, HDL, glucose, and triglycerides, among others.

Figure 3:
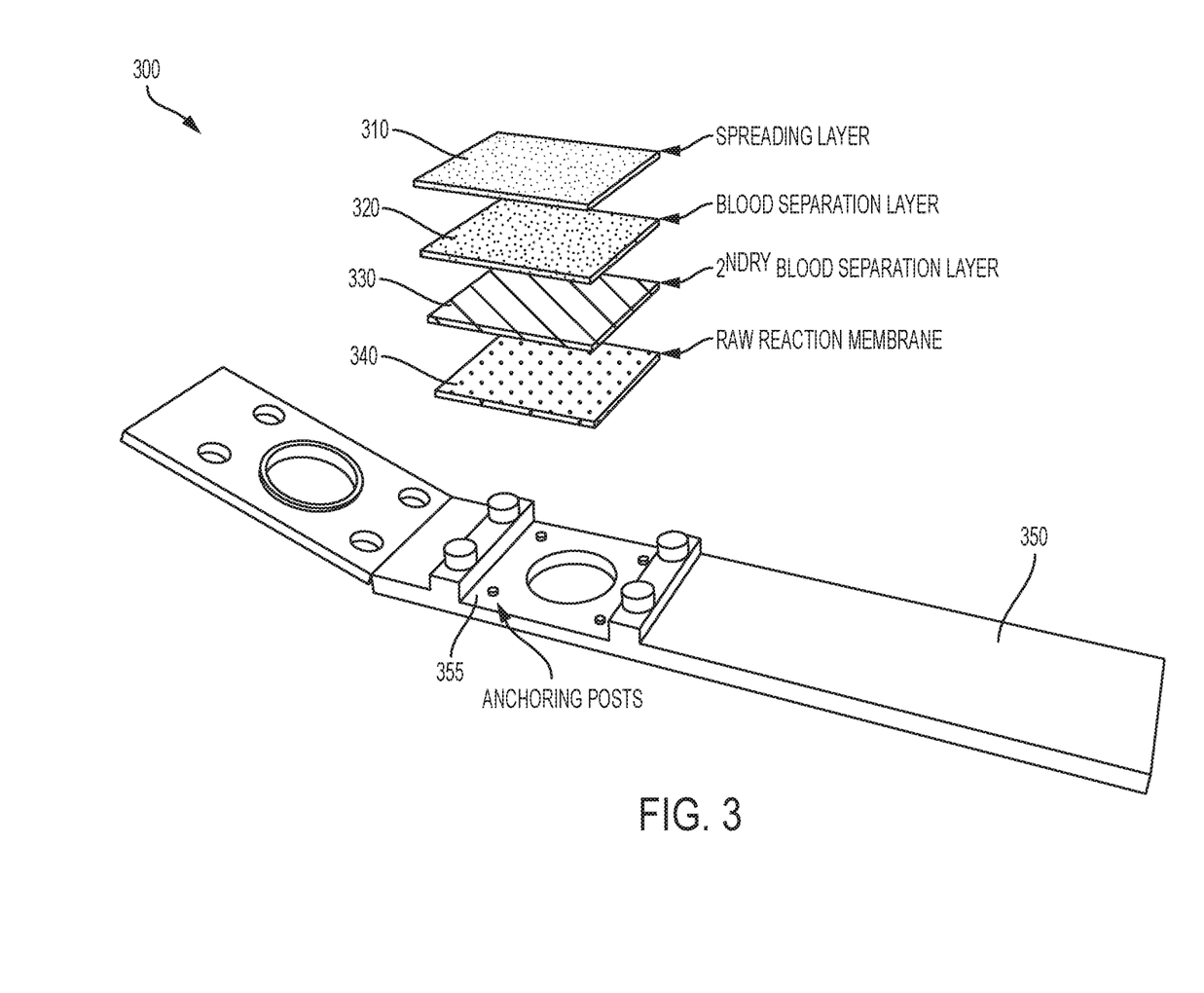
FIG. 3 shows one embodiment of a test strip for use with a premix step.
Figure 4:
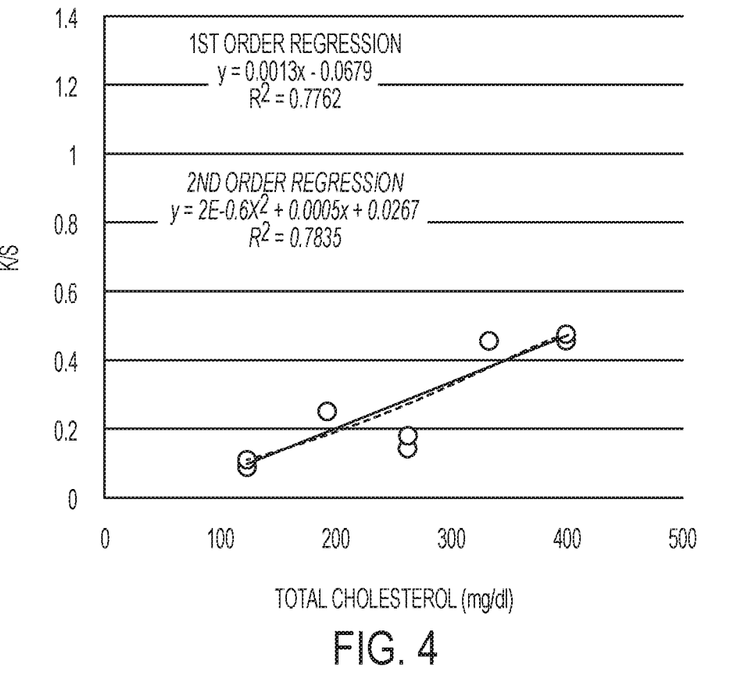
FIGS. 4-10 show graphs illustrating the dose response at increasing cholesterol concentrations tested in one embodiment of a reagentless test strip with a premixed solution applied.
Figure 5:
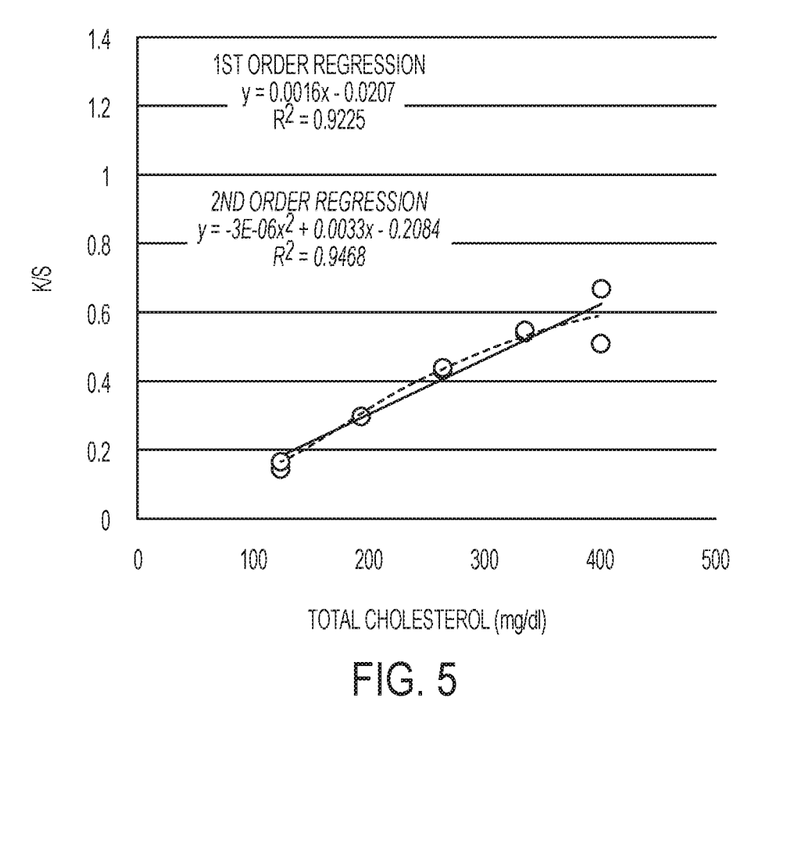
Figure 6:
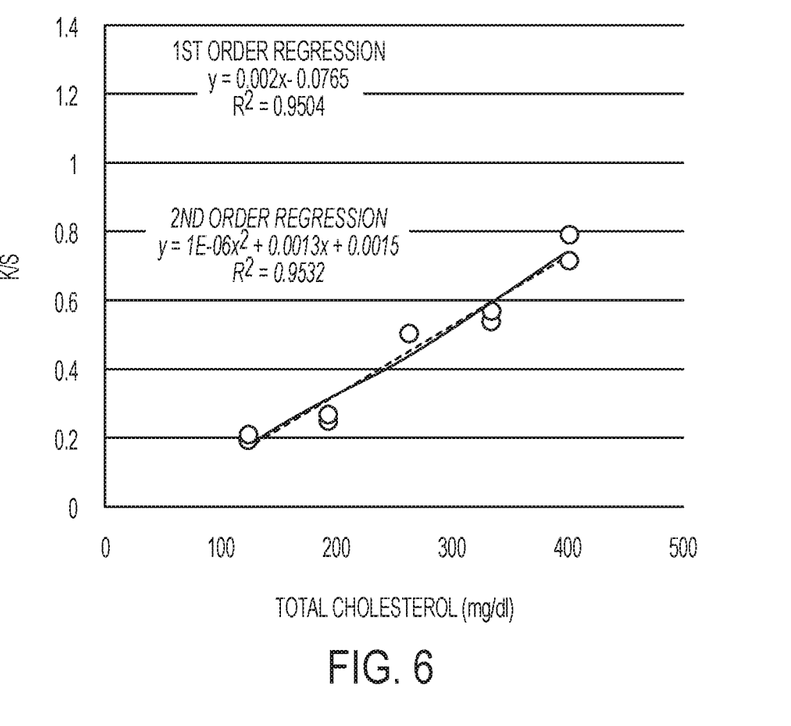
Figure 7:
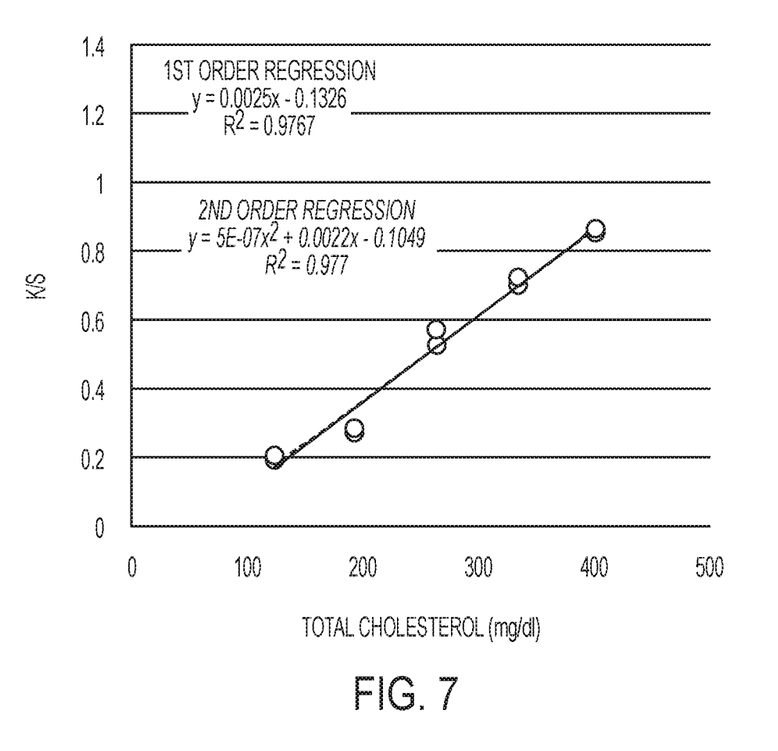
Figure 8:
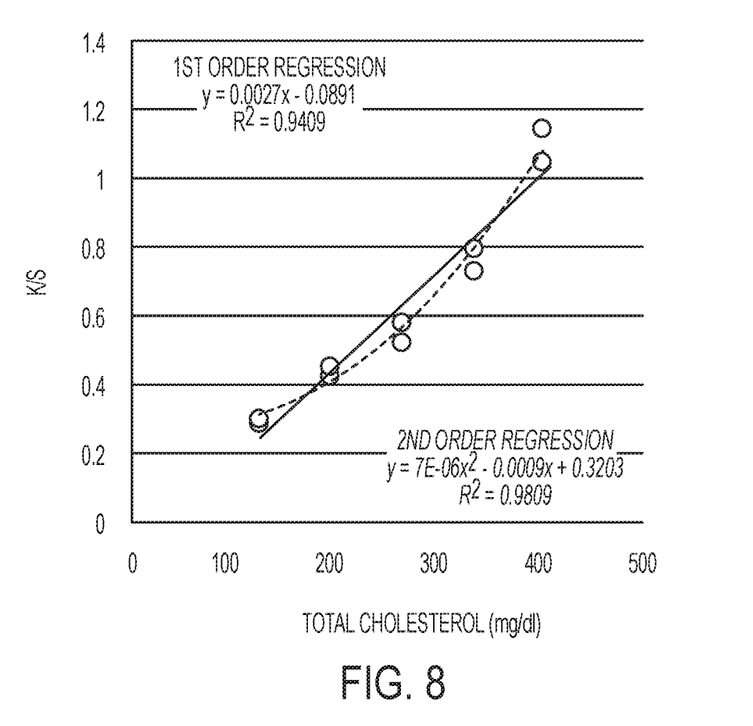
Figure 9:
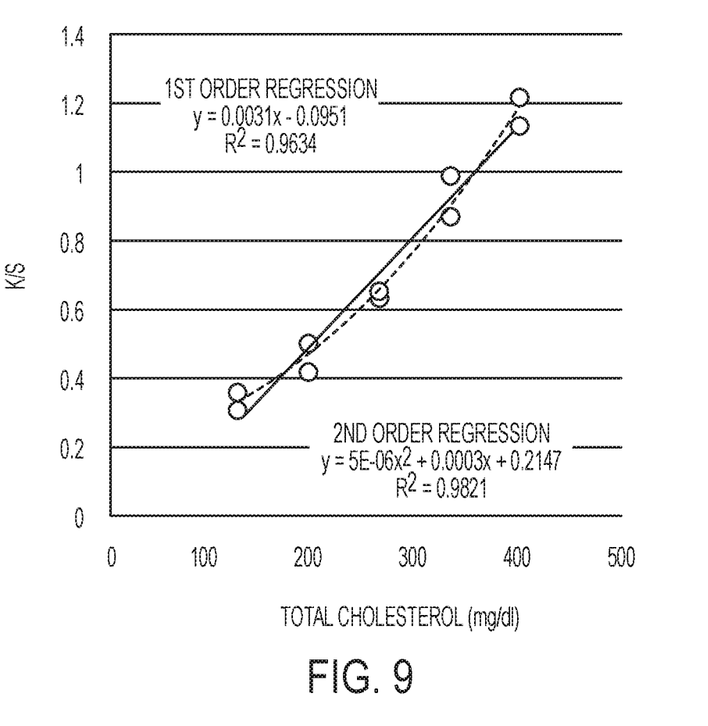
Figure 10:
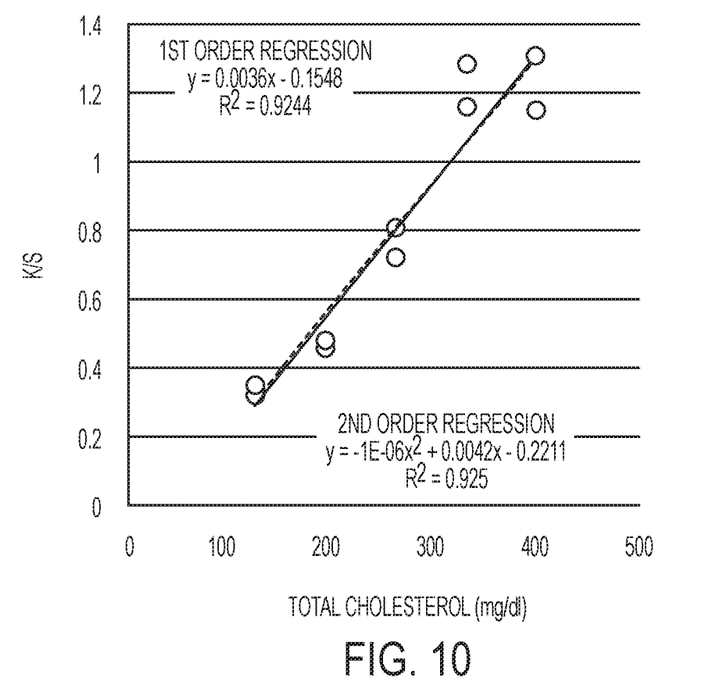

Embodiments of the single strip will be constructed in such a way that they will contain certain elements that will have the ability to spread the whole blood using a spreading layer, a blood separation layer made of borosilicate glass fiber membrane impregnated with lectins and other RBC capturing agents, and a secondary blood separation later. FIG. 3 shows one embodiment of a test strip for use with a premix step. The test strip 300 includes a spreading layer 310, a first blood separation layer 320, a second blood separation layer 330, a reaction layer 340 that does not contain any reagents, and casing 350 with anchoring posts 355. This is just an exemplary embodiment of a test strip 300, and the test strip 300 in alternative embodiments may have merely a single membrane or layer. Alternatively, the test strip may be a single reaction layer with one or more RBC (red blood cell) separation layers. Alternatively, a spreading layer additionally may be included with any of the above configurations. In one configuration, spreading layer 310 is Petex™, slit to 0.20×0.180 inches. In one configuration, the first blood separation layer 320 is Tuffglass™ slit to 0.20×0.180 inches. Optionally, this layer is impregnated with lectins and other RBC capturing agents. In one configuration, the second blood separation layer 330 is CytoSep™ 1660, slit to 0.20×0.180 inches. In another configuration, the reaction layer 340 is 0.45 A Biodyne Membrane™, slit to 0.20×0.180 inches.

In some configurations, the optical reader may be replaced with a handheld electronic device such as a cell phone, PDA, or tablet. In some configurations, a blank test strip module in a casing that eliminates outside light, except from a single light source from lighting the test strip, may be provided that fits over the camera of the handheld electronic device. Therefore, a standard module with spreading and RBC separation layers may be provided at little cost; then each module may be configured by providing the corresponding premix collector and mixer, the collector and mixer containing reagents for testing for the analyte of interest.

Results of prototypes including a premix step and a reagentless strip are discussed below.

Example 1

A total cholesterol (TC) formulary was prepared using Polymer Technology Systems, Inc., work instruction. To a 100 µL TC reaction formulation was added serum at various TC concentrations (see Table 1) at various volumes (see Table 2). The solution was mixed via vortex. 12 µL of the final solution then were dosed on the test strip. Tables 1 and 2 show the results from this example.

TABLE 1

| Serum Levels | Serum TC Concentrations (mg/dL) |
|---|---|
| 1 | 123 |
| 2 | 192 |
| 3 | 263 |
| 4 | 333 |
| 5 | 400 |

TABLE 2

| Volume of TC reagent (µL) | Volume of Serum (µL) | Total Volume (µL) | Volume dosed on Strip (µL) | "Effective Sample Volume dosed" (µL) |
|---|---|---|---|---|
| 100 | 20 | 120 | 12 | 1.85 |
| 100 | 25 | 125 | 12 | 2.30 |
| 100 | 30 | 130 | 12 | 2.77 |
| 100 | 35 | 135 | 12 | 3.23 |
| 100 | 50 | 150 | 12 | 4.61 |
| 100 | 75 | 175 | 12 | 6.92 |
| 100 | 100 | 200 | 12 | 9.23 |

The graphs of FIGS. 4-10 show the dose response at increasing cholesterol concentrations when the "effective" samples size increases from 1.85 to 9.4 µL. For each graph, a linear regression and a second order polynomial equation and line has been computed to determine the curve-fitting equation for the graph. Graphs of FIGS. 4-8 all show better correlation (R2) to a polynomial fit line than to a linear regression line. While Graphs 7 and 10 both show there is no difference between the first and second ordered curve, the correlation in graph 10 is much lower compared to the correlation in graph 7 (R2 of 0.92 vs. 0.97). This indicates that the "effective" volume condition of 3.4 µL of sample is optimal to yield a linear dose response across the dynamic range of the assay.

Kinetic Data

Figure 11:
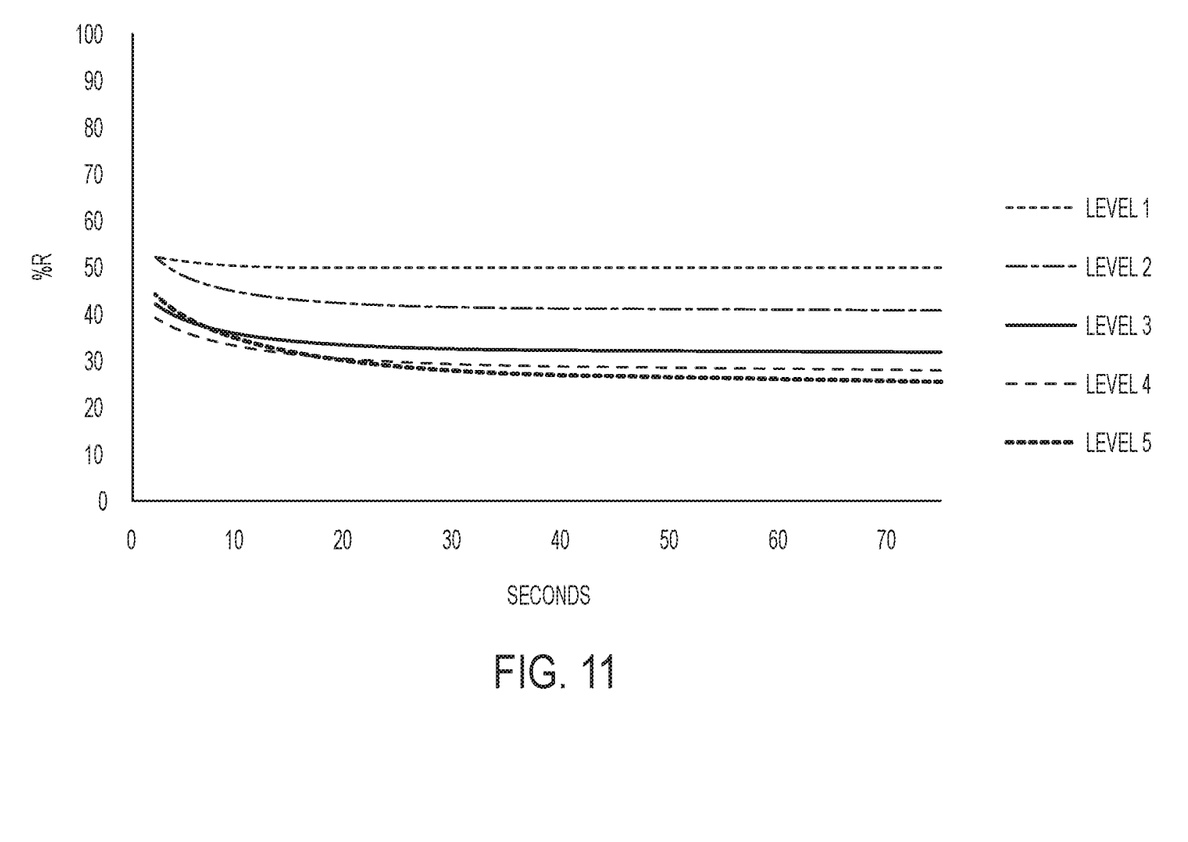
FIGS. 11 and 12 shows kinetic curves for a 3.2 µL "effective" sample size in a dry test strip compared to a strip where the reagents have been impregnated in the membrane.
Figure 12:
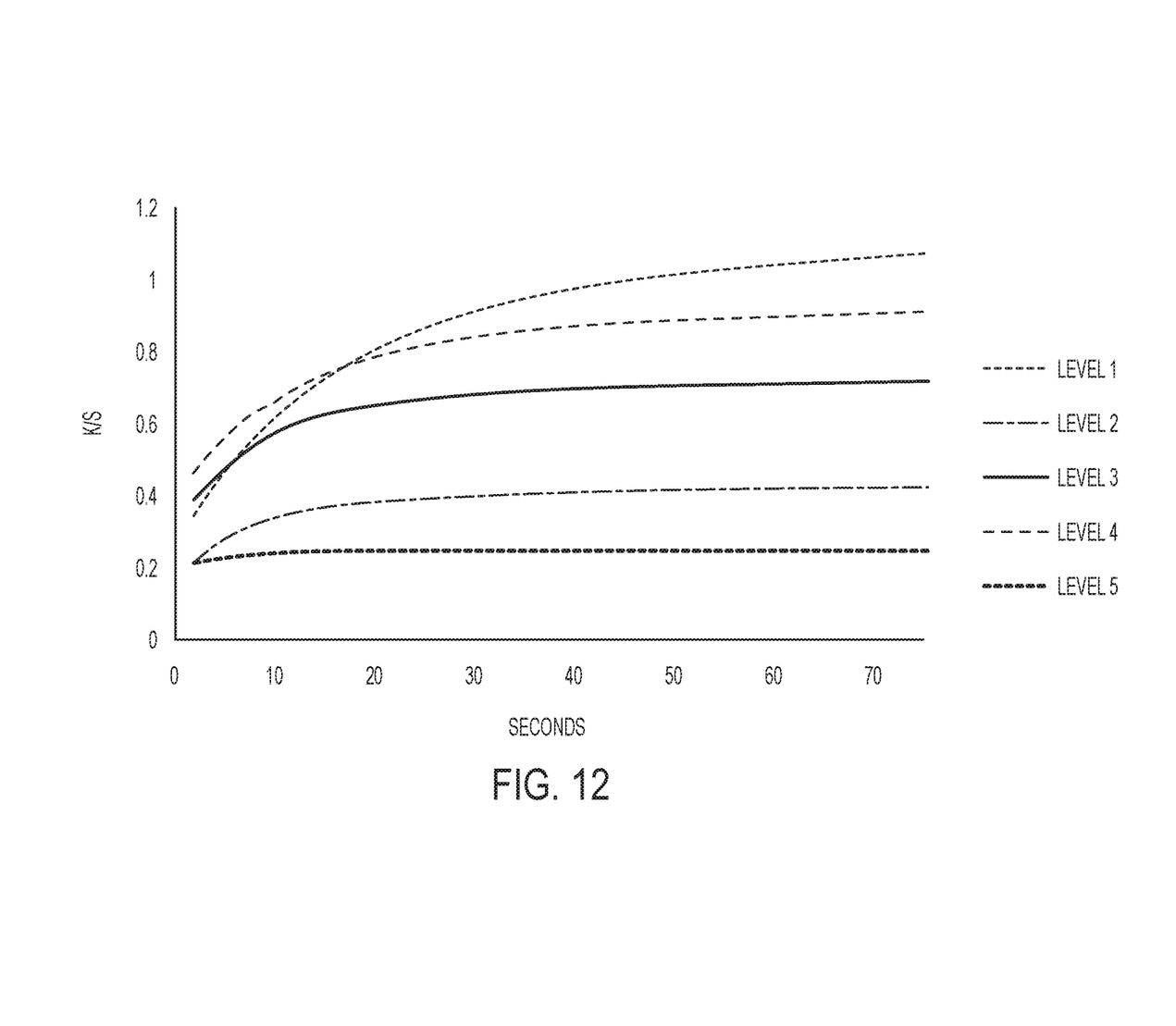

The data in FIGS. 11 and 12 shows the kinetic curve for a 3.2 µL "effective" sample size compared to a strip where the reagents have been impregnated in the membrane.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof. Note that, although particular embodiments are shown, features of each may be interchanged between embodiments.

What is claimed as new and desired to be protected by Letters Patent of the United States is:

1. A system for detecting an analyte with a reagentless dry test strip, comprising:
   a dry test strip including a reagentless membrane which does not include any reagents;
   a collector for collecting a blood sample from a user;
   a mixer separate from and shaped to mate with the collector, the mixer having a first condition separate from the collector and a second condition mated with the collector; and
   one or more reagents in the liquid form located in the mixer for forming a mixture with the blood sample when the mixer is mated with the collector, the one or more reagents effective to cause a color change of the mixture while within the mixer prior to dosing the mixture to the dry test strip,
   the reagentless membrane of the dry test strip being configured for receiving the mixture from the mixer.

2. The system of claim 1, wherein the collector includes a capillary tube.

3. The system of claim 1, wherein the mixer is shaped to seal with the collector when the collector is inserted into the mixer.

4. The system of claim 1, wherein the dry test strip includes a spreading layer.

5. The system of claim 1, wherein the dry test strip includes a first red blood cell separation layer.

6. The system, of claim 5, wherein the dry test strip includes a second red blood cell separation layer.

7. The system of claim 1, wherein the one or more reagents provide for the testing of total cholesterol.

8. The system of claim 7, wherein the one or more reagents include cholesterol esterase, cholesterol oxidase, horseradish peroxidase, and quinoneimine chromophore precursors selected from the list consisting of: 4-amino antipyrine (4-AAP) and N-Ethyl-N-(2-hydroxy-3-sulfopropyl)-3,5-dimethylaniline, sodium salt and monohydrate (MAOS).

9. The system of claim 1 and further comprising:
   a casing receiving the dry test strip and defining an application window; and
   a first red blood cell separation layer received in the casing and positioned closer to the application window than the reagentless membrane.

10. The system of claim 1 and further comprising: a casing receiving the dry test strip and defining a reading window, the reagentless membrane being positioned adjacent to the reading window; and a first red blood cell separation layer is received in the casing and positioned closer to the reading window than the reagentless membrane.

* * * * *